United States Patent [19]

Jenkins

[11] 4,242,107
[45] Dec. 30, 1980

[54] APPARATUS FOR THE SEPARATION OF A CONSTITUENT FROM AN ATMOSPHERE

[76] Inventor: Anthony Jenkins, Analytical Instruments Limited, London Rd., Pampisford, Cambridge, England

[21] Appl. No.: 931,402

[22] Filed: Aug. 7, 1978

Related U.S. Application Data

[63] Continuation of Ser. No. 800,054, May 24, 1977, abandoned.

[30] Foreign Application Priority Data

May 25, 1976 [GB] United Kingdom ............... 21551/76

[51] Int. Cl.³ .......................................... B01D 53/08
[52] U.S. Cl. ........................................ 55/18; 55/60;
55/67; 55/78; 55/181; 55/208; 55/390
[58] Field of Search ................. 55/18, 67, 77, 78, 197, 55/208, 386, 387, 390, 521, 524, 486, 489, 60, 181; 210/31 C, 198 C

[56] References Cited

U.S. PATENT DOCUMENTS

| | | | |
|---|---|---|---|
| 2,891,630 | 6/1959 | Hall et al. | 55/197 |
| 3,016,106 | 1/1962 | Luft | 55/197 |
| 3,077,103 | 2/1963 | Heaton | 55/197 X |
| 3,078,647 | 2/1963 | Mosier | 55/197 |
| 3,140,936 | 7/1964 | Schwartz | 55/390 X |
| 3,201,921 | 8/1965 | Heyes | 55/386 X |
| 3,257,781 | 6/1966 | Debbrecht et al. | 55/197 |
| 3,374,607 | 3/1968 | Fisher et al. | 55/197 X |
| 3,417,548 | 12/1968 | Thompson | 55/67 |
| 3,578,757 | 5/1971 | Samuilov et al. | 55/197 X |
| 3,656,277 | 4/1972 | Slingerland | 55/197 X |
| 3,678,656 | 7/1972 | Brunnee et al. | 55/197 |
| 3,695,003 | 10/1972 | Bednarski | 55/386 X |
| 3,780,498 | 12/1973 | Wenner | 55/390 X |
| 3,800,859 | 4/1974 | Norback | 55/390 X |
| 3,847,578 | 11/1974 | Munters | 55/390 |
| 3,856,681 | 12/1974 | Huber | 55/386 X |
| 3,905,788 | 9/1975 | Alliger | 55/489 |
| 4,012,206 | 3/1977 | Macriss et al. | 55/390 X |

FOREIGN PATENT DOCUMENTS

1339621  12/1973  United Kingdom ...................... 55/390

*Primary Examiner*—Robert H. Spitzer
*Attorney, Agent, or Firm*—Anthony J. Casella; Michael A. Stallman

[57] ABSTRACT

An apparatus for sampling an atmosphere for the presence of a constituent in which a flow of the atmosphere is first drawn through a trap capable of releasably absorbing the constituent and the trap is then passed through a carrier gas stream which removes and conveys the constituent into a detector. The trap can comprise a rotatable disc of wire mesh which cuts continuously across a flow of the atmosphere and a carrier gas flow. The volume flow rate of the atmosphere is greater than that of the carrier gas so giving a large concentration gain of the constituent in the carrier flow. The apparatus can be used for detecting the presence in the atmosphere of vapors emanating from explosives and for this purpose the carrier gas flow can be directed into an electron capture detector.

6 Claims, 5 Drawing Figures

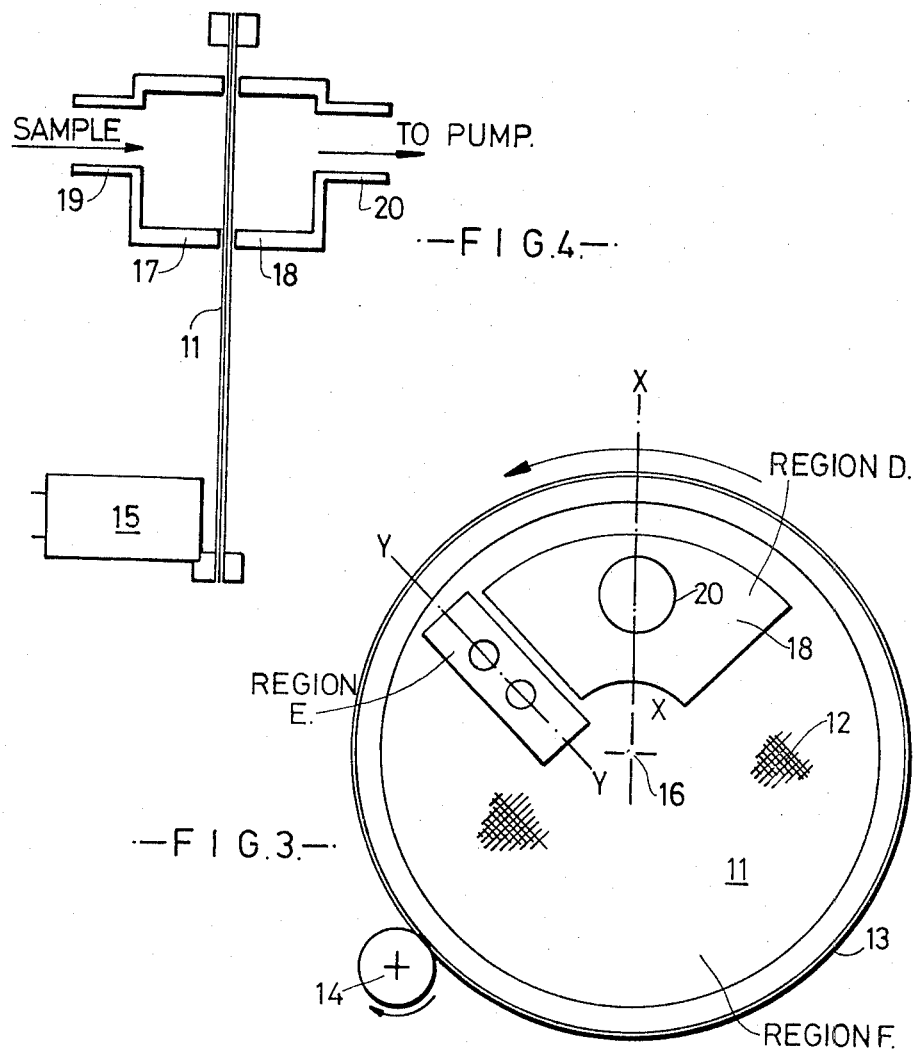
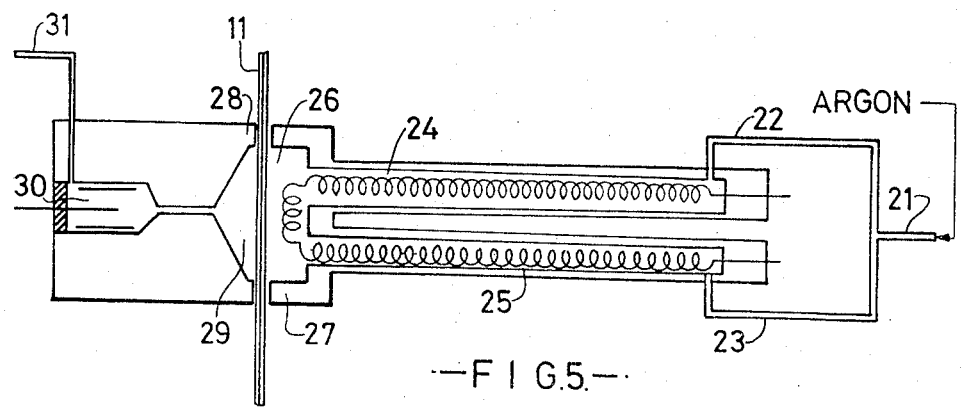

APPARATUS FOR THE SEPARATION OF A CONSTITUENT FROM AN ATMOSPHERE

This is a continuation of application Ser. No. 800,054, filed May 24, 1977, now abandoned.

The present invention concerns an apparatus for the separation of a component of interest from a multi-component gaseous sample.

British Pat. No. 1,339,621 discloses an apparatus for separating individual components from a multi-component sample comprising a column formed from a material which is non-absorbent to the components of the sample, a sample inlet adjacent one end of the column, an outlet adjacent the other end of the column, and an exhaust port and a carrier gas inlet port intermediate the sample inlet and said outlet with the exhaust port located between the sample inlet and the carrier gas inlet port, means for continuously moving a belt formed from or containing a chromatographic material through the column from the sample inlet end to the outlet end, and means for heating the column at least over the lengths thereof between the exhaust port and the carrier gas inlet port and the carrier gas inlet port and the outlet respectively such that the temperature of the column increases from the one end to the other end thereof.

In the prior art apparatus above mentioned a sample introduced into the column is separated into its individual components and the least volatile of the components is carried by the belt into the vicinity of the outlet from where it is conveyed by the carrier gas, preferably into a detector.

The present invention seeks to provide an apparatus capable of sampling larger flows than hitherto and for transferring sample continuously into a relatively small carrier flow whereby to obtain a large concentration gain.

According to the present invention an apparatus for separating a component of interest from a multi-component gaseous sample comprises an endless movable member having a plurality of channels therethrough, each channel constituting a trap for releasably retaining the component of interest, means for moving the member across at least two regions namely, a first region at which a flow of the gas sample is drawn through the traps and a second region at which the traps are heated and subjected to a carrier gas flow whereby to expel the trapped component.

The invention will be described further, by way of example, with reference to the accompanying drawings; in which:

FIG. 3 is a diagrammatic end view of a second embodiment of an apparatus according to the invention;

FIG. 4 is a section on line X—X in FIG. 3; and

FIG. 5 is a section on line Y—Y in FIG. 3.

Figure 1:
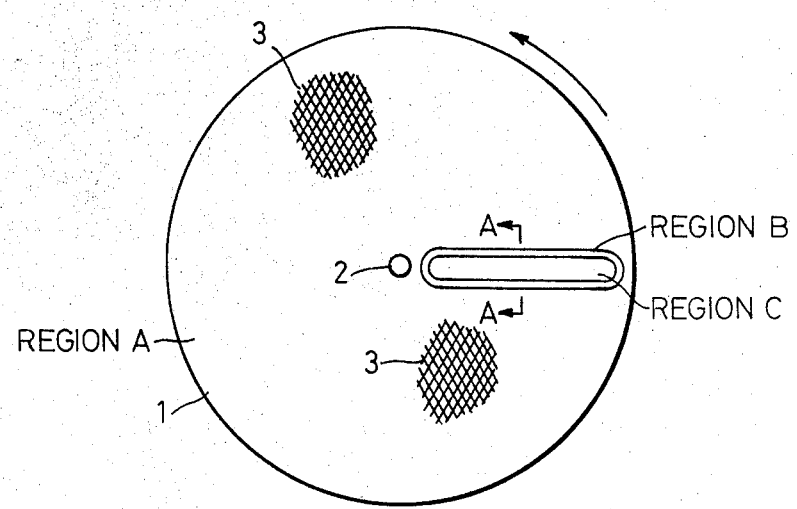
FIG. 1 is a diagrammatic end view of a first embodiment of an apparatus according to the invention.
Figure 2:
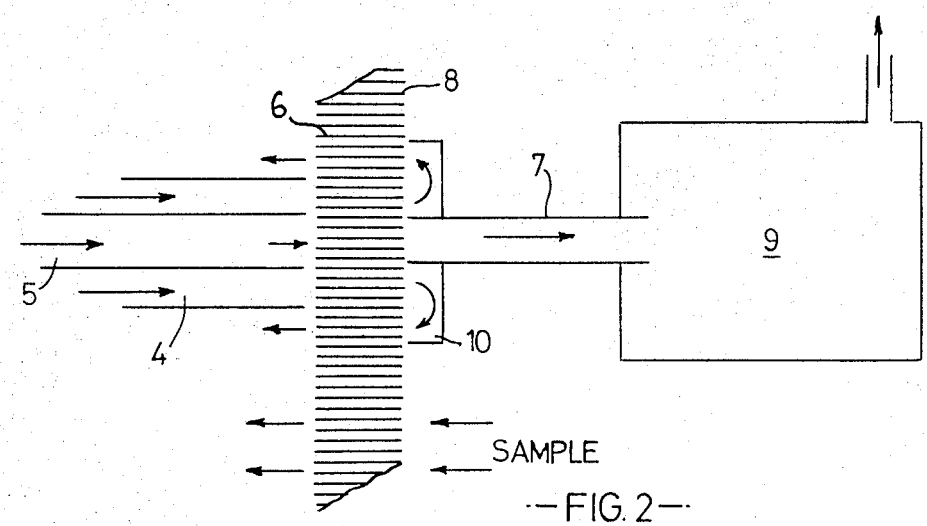
FIG. 2 is a diagrammatic enlarged section on line A—A in FIG. 1.

In FIGS. 1 and 2 a disc 1, rotatable about its axis 2, comprises a matrix of tubular channels or traps 3, each channel or trap constituting a short chromatographic column. Thus, for example, each channel or trap 3 can be coated with a coating material capable of releasably absorbing a particular gaseous constituent or component flowing therethrough. The disc can, for example, be formed from metal, such as stainless steel, glass or ceramic. The faces of the disc are substantially plane and parallel. The disc can be arranged within a conduit which is coupled to a pump so as to draw a stream of sample through the channels. Rotation of the disc about its axis can be achieved by means of an endless belt passing about the periphery of the disc, which can be grooved, and a drive pulley of a motor. Conveniently, the motor and belt are arranged within a support frame for the disc.

During each complete revolution of the disc 1, each trap 3 moves through three regions which for convenience are denoted regions A, B and C. These are marked in FIG. 1.

Region A comprises a major part of the disc and is exposed to sample flow. Regions B and C constitute means for conducting carrier gas flows to the traps, region B surrounding region C.

As seen from FIG. 2, regions B and C are formed by channels 4 and 5 respectively which terminate at one end in close proximity to face 6 of the disc 1. The opposite ends of the channels are connected to a carrier gas supply. A channel 7 at the opposite face 8 of the disc 1 and in alignment with the channel 5 communicates with a detector, for example an electron capture detector. A compartment 10 is disposed about the end of the channel 7 adjacent face 8 of the disc, the area of the compartment in a plane parallel to the plane of the disc being greater than the area of the channel 4.

In use, the disc 1 is rotated about its axis 2 and a sample gas flow is drawn through region A of the disc by means of the pump. In passing through the traps 3 components of interest are absorbed and retained by the coating layer applied to the traps. At region B the traps receive a flow of a purge gas, such as argon, delivered through conduit 4. The argon flow purges the traps to remove volatile components trapped therein. The traps then pass across region C at which a supply of hot carrier gas, which can again be argon, from the conduit 5 liberates any low volatility component which might be retained in the traps. The liberated component is carried by the hot carrier gas along channel 7 into the detector. The detector exhaust is conveniently connected to a suction pump.

As seen from FIG. 2, the purge gas exits on the pump side of region A of the disc and each trap in moving across regions B and C receives a forward and reverse flow of purge gas. The flow is reversed in the compartment 10 and the reverse flow provides a seal at the faces of the disc. Sample air cannot leak into the flow to the detector and the arrangement avoids the use of complicated physical seals between the disc and the channels for the carrier gas and the channel to the detector. The arrangement in effect is self-sealing.

The speed of rotation of the disc 1 is determined by the time required to ventilate each trap of the component of interest. Alternatively, or in addition, means can be provided for adjusting the flows of the carrier gas. The temperature of the hot carrier gas flow is chosen to release the component of interest from the traps.

The hot carrier gas can be at a temperature of 200° C. or more. It is helpful to employ auxiliary means to heat the traps as they move across region C so as to avoid cold spots in the flow path and to ensure that the temperature remains at the required value to release the trapped component or components. For example, electrodes or eddy current means can be applied to the traps moving across region C. Alternatively it is possible to utilize a cold gas flow to region C and to rely on trap heating to release the component. However, a hot carrier gas flow is preferred.

FIGS. 3 to 5 illustrate a second and preferred embodiment of the invention. In this embodiment a disc 11 is formed from a plurality of superimposed wire mesh grids 12. Conveniently three wire grids are employed and each grid can be coated with a material, for example active carbon, capable of releasably absorbing a particular gaseous component in a gas flow passing through the disc. The periphery of the disc of superimposed grids is clamped or otherwise secured to a gear ring 13 which engages a gear wheel 14 of a drive motor 15 to rotate the disc about its axis 16.

As in the case of the embodiment of FIGS. 1 and 2 the wire mesh grids form a plurality of traps and during a complete revolution of the disc each trap moves across regions D, E and F. At region D, a sample gas flow is drawn through the traps. At region E, a heated carrier or purge gas is passed through the traps to release any trapped component into a detector assembly. Over region F the grid is allowed to cool before returning to region D.

At region D, two arcuate open ended compartments 17 and 18 are arranged in alignment at opposite sides of the disc 11. The open ends of the compartments are in close proximity to the faces of the disc. Sample to be tested is drawn into the compartment 17 through an inlet 19 and through the wire mesh grids by means of a suction pump connected to an outlet 20 from the compartment 18. The sample can be drawn from the atmosphere.

On leaving region D the traps immediately enter region E where hot carrier gas, conveniently argon, is drawn through the traps. With reference to FIG. 5, an inlet 21 is connected to a source of argon. The inlet 21 divides into two branches 22 and 23 which communicate with respective heater compartments 24 and 25. In flowing along the compartments the gas is heated to a required temperature and emerges into a chamber 26 at one side of the disc 11. As shown the heater element also extends across the chamber 26. The chamber 26 is bounded by a continuous flange or lip 27 and a similar flange or lip 28 is provided about a chamber 29 on the opposite side of the disc. The flanges 27 and 28 are positioned in close proximity to the faces of the disc 45 such that the disc will just pass between the flanges with a minimum gap therebetween.

The pressure of the argon gas flow is arranged to be slightly greater than atmospheric pressure with the result that a small amount of argon will flow outwardly between the flanges 27 and 28. This purges the traps prior to their entry into region E and effectively seals region E against inward diffusion of atmosphere.

The hot argon flow is drawn through the traps at region E to release any component contained in the traps. The flow is drawn into a detector 30, such as an electron capture detector, which can detect the presence of the component in the flow.

Outlet 31 from the detector is connected to a suction pump which can be the same pump as that connected to the outlet from region D.

On leaving region E the disc passes through region F at which the grids are exposed for cooling. Region F extends over a major portion of the area of the disc.

If required, for example in conditions of severe background contaminants in the sample flow, a separate purge region can be arranged between regions D and E. Thus a supply of cold, clean gas, which can be argon, can be directed through the disc to purge the traps of unwanted components prior to entry into region E. Such an arrangement would be similar to that described with reference to FIGS. 1 and 2. However in the majority of applications it is not necessary to employ a cold purge and the traps can pass directly from region D into region E.

As mentioned active carbon can be employed in the traps. However other absorbants can be used such as a polar liquid phase which can selectively absorb polar material and can produce a more selective trap.

As seen from FIG. 5, in addition to being heated by the hot argon flow the traps are also subjected to direct radiant heat from the portion of the heater element within the compartment 26.

The invention provides an apparatus capable of functioning as a continuous trap for extracting or capturing certain components from a large gas flow, which can be an air flow, and transferring the components into a relatively small release gas stream, again on a continuous basis, whereby to obtain a large concentration gain. The absorbant employed in the trap and also the type of detector will be determined by the nature of the component or components of interest and will be apparent to any person skilled in this art. The release gas can be an inert gas, such as argon or nitrogen, which can be passed directly into the detector which can be an electron capture detector. As examples only, the apparatus can be used to detect the presence in the atmosphere of vapours from explosive compounds and vapours emitted by and characteristic of certain drugs. Due to the concentration gain resulting from transferring the constituents from a large flow rate to a small carrier flow the apparatus is sensitive to minute quantities present in the atmosphere.

I claim:

1. A method of continuously detecting a component of interest from a multi-component gaseous sample which comprises rotating a disc having a matrix of channels extending between the opposite faces thereof about its axis normal to said faces to move the channels through at least first and second regions, drawing a sample flow through the channels moving across the first region to trap the component of interest, arranging carrier gas flow means at the second region close to but spaced from the opposite faces of the disc to provide clearances for the rotary movement of the disc therebetween, subjecting the channels to a flow of carrier gas and heat at the second region to expel the component of interest, channeling said expelled flow of carrier gas and component of interest to a detector means for detecting the component of interest in the carrier gas flow while simultaneously allowing a portion of the flow at the second region to escape outwardly through the clearances to create a gaseous barrier against ingress of atmosphere into the second region, the flow of sample through the first region being greater than the flow of carrier gas through the second region whereby to obtain a concentration gain of the component of interest in the carrier gas flow from the second region.

2. An apparatus for effecting the continuous detection of a component of interest from a multi-component gaseous sample comprising: a detector means; and a separation means, operatively connected to said detector means, for continuously separating said component of interest from said multi-component gaseous sample, said separation means including a rotatable disc having a matrix of channels between the opposite faces of the disc, each channel constituting a trap for releasably retaining the component of interest, means for rotating the disc about its axis normal to said faces to move the channels through at least first and second regions, means at the first region to draw a flow of sample through the channels moving across the first region to trap the component of interest, means at the second region to draw a flow of carrier gas through the channels moving across the second region and into said detector means and means for heating the channels to release the component of interest, with the flow means at the second region being close to but spaced from the opposite faces of the disc to provide clearances for the rotary movement of the disc therebetween and to enable a portion of the carrier flow to escape outwardly through said clearances whereby to provide a gaseous barrier against ingress of atmosphere into the second region.

3. An apparatus according to claim 2 in which the first region comprises two aligned, arcuate, open-ended, compartments disposed one at each face of the disc and extending angularly over a portion of the disc, the end of each compartment adjacent the disc being open with the opposite end of one of the compartments being open to the atmosphere and the opposite end of the other compartment being connected to a suction pump.

4. An apparatus according to claim 3 in which the second region comprises two aligned, open-ended chambers disposed one at each face of the disc with the boundary walls of the chambers in close proximity to the faces of the disc, means for connecting one of the chambers to a supply of carrier gas, means for heating the supply of carrier gas to said one chamber and means for connecting the other chamber to said detector.

5. An apparatus according to claim 2 in which the disc comprises a grid of superimposed meshes.

6. An apparatus according to claim 2 including a further region interposed between said first and second regions and means for drawing a supply of a cold purge gas through the channels at said further region.

* * * * *